United States Patent [19]

Moracchini et al.

[11] Patent Number: 5,756,884
[45] Date of Patent: May 26, 1998

[54] DEVICE FOR DETERMINING CHARACTERISTICS OF PETROLEUM FLUID SAMPLES FOR EXAMPLE ON A PRODUCTION SITE

[75] Inventors: Gerard Moracchini, Antilly; Emmanuel Behar, Jouy-le-Moutier; Jose Sanchez, Viarmes, all of France

[73] Assignees: Institut Francais du Petrole, Rueil-Malmaison; Societe ROP, Argenteuil, both of France

[21] Appl. No.: 647,964
[22] PCT Filed: Sep. 29, 1995
[86] PCT No.: PCT/FR95/01263
 § 371 Date: Sep. 6, 1996
 § 102(e) Date: Sep. 6, 1996
[87] PCT Pub. No.: WO96/10745
 PCT Pub. Date: Apr. 11, 1996

[30] Foreign Application Priority Data

Sep. 30, 1994 [FR] France .................. 94 11817

[51] Int. Cl.$^6$ ........................................ G01N 7/14
[52] U.S. Cl. .................. 73/61.44; 73/61.46; 73/61.47
[58] Field of Search ............. 73/53.01, 54.02, 73/61.41, 61.43, 61.44, 61.46, 61.47, 61.48, 61.76, 61.78, 64.45, 64.55; 374/54, 55, 27, 16; 356/436; 250/564, 577, 227.29, 227.2, 576, 573

[56] References Cited

U.S. PATENT DOCUMENTS

| | | | |
|---|---|---|---|
| 2,380,082 | 7/1945 | Sloan | 73/19.1 |
| 2,662,393 | 12/1953 | Rzasa | 73/19.1 |
| 4,658,637 | 4/1987 | Ollivaud et al. | 73/61.41 |
| 4,752,131 | 6/1988 | Eisenlauer et al. | 250/573 X |
| 4,783,989 | 11/1988 | Reed | 73/64.45 |
| 5,022,259 | 6/1991 | Lee et al. | 73/64.45 |
| 5,287,168 | 2/1994 | Poucher et al. | 250/573 X |

*Primary Examiner*—Michael Brock
*Attorney, Agent, or Firm*—Antonelli, Terry, Stout, & Kraus, LLP

[57] ABSTRACT

A rigid body comprising two cylindrical chambers (14, 15) with a pointed bottom for example, connected to each other by a fine line controlled by a valve V5, is fixed in a thermostat-controlled enclosure (7). Two rods (18, 17) forming pistons, provided with prestressed seals (J), can slide in these chambers, separately or coupled with one another. Their shape is suited to that of the bottom of the chambers. These rods are moved by shifting vertically hangers (12, 13) integral therewith, by means of threaded rods (8, 10) driven into rotation on demand by motors (ME1, ME2). A control unit comprising two optical display and locating blocks (19, 20) running right through the body near the bottom of the lower chamber (14), pressure, temperature and displacement detectors, under the control of a micro-computer, allows precise thermodynamic measurements to be achieved on substance samples at high pressure and temperature values. A gasometer is preferably placed in enclosure (7). According to another implementation mode, the upper chamber can be replaced by a gasometer for sample validation operations.

27 Claims, 6 Drawing Sheets

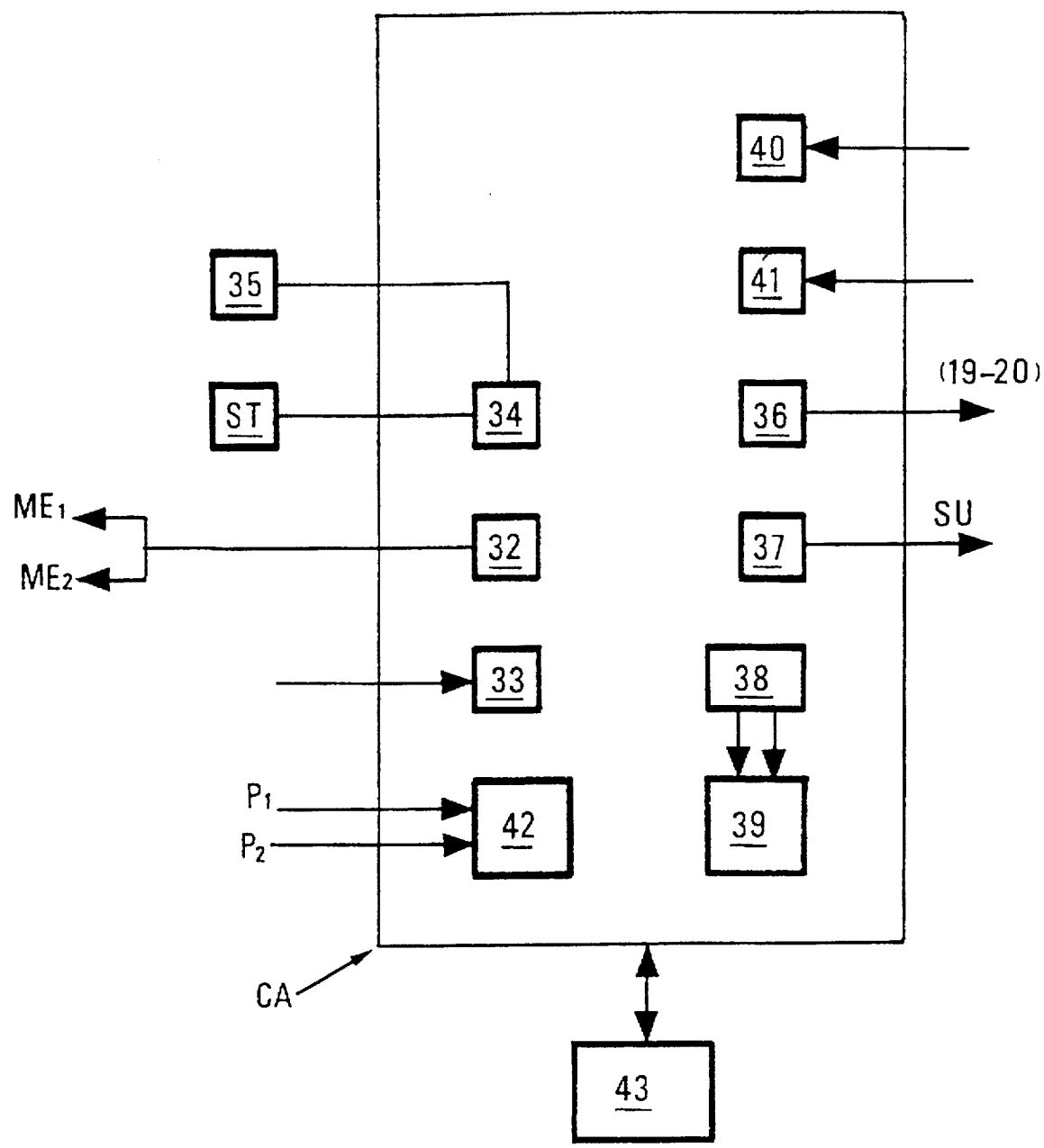

5,756,884

DEVICE FOR DETERMINING CHARACTERISTICS OF PETROLEUM FLUID SAMPLES FOR EXAMPLE ON A PRODUCTION SITE

FIELD OF THE INVENTION

1. Background of the Invention

The present invention relates to a device for determining, on a production site, characteristics of fluid samples extracted from the subsoil, notably from petroliferous areas, and more particularly to a compact site device that can be easily transported to production sites.

2. Description of the Prior Art

It is customary to study the thermodynamic properties of samples extracted from wellbores with a view to developing underground deposits of effluents such as petroleum effluents. A good knowledge of these thermodynamic properties allows assessment of the subsurface reserves, to optimize the production installation or to specify the methods of operation. The thermodynamic properties are calculated by using composition models into which data obtained by analyzing the samples are integrated.

A so-called "PVT" type analysis method for example allows measurement of the behavior of samples including certain parameters of which, such as pressure and temperature, are varied for example from values replicating those existing at their depth in a well to those prevailing at the surface. Methods of analysis of this type make it possible to measure important properties such as the "bubble point" indicating the appearance of a gas phase in the sample tested, the compressibility coefficient, the viscosity, the density, the GOR, etc. as it is known.

The Assignee's French patent 2,666,415 describes a device for performing thermodynamic measurements on small-volume samples in a laboratory or on a site. This device comprises a thermostat-controlled enclosure, a supporting structure with two plates on either side of a transparent sapphire block for example and two small-section cylindrical chambers defined by two sliding pistons moved in both chambers by mechanical drive means including threaded rods driven into rotation by shafts coupled with motive means. Seals are arranged in grooves provided in the wall of the two chambers, around both pistons. The first chamber is partly visible through the transparent block, and it ends in a bevel at the top of which opens a line communicating with the second chamber by means of a valve. A capillary tube connects the two chambers to each other and allows viscosity measurements to be performed on the samples. On account of its compactness, this prior device can be easily transported to the sampling sites.

SUMMARY OF THE INVENTION

The invention allows measurement directly on a production site of characteristics of fluid samples extracted from the subsoil, notably from petroliferous areas. It comprises, in a thermostat-controlled enclosure, a body including a first chamber and a second chamber placed above the first one, the first chamber at least comprising a pointed end, and the volumes of these two chambers being variable by shifting mobile elements in two cylinders, means for moving the two mobile elements, means for transferring fluids into or out of the chambers, and controlled communication means between the two chambers.

The device according to the invention allows performing on site extensive thermodynamic measurements by relieving operators of many operating sequences. It also allows samples to be validated in order to check that they are really representative of the samplings that have been achieved, prior to sending them to a central laboratory for more complete analyses.

These previous measurements and analyses performed on site with samples of very small volume allow avoiding the long and costly conventional solutions consisting of sending systematically samples to a distant laboratory, which must sometimes be repeated when it turns out that the samples are not valid and representative. Using the device according to the invention therefore allows saving of time and making significant savings.

The device according to the invention allows for example, in the case of oil type petroleum samples, measurement of their GOR (gas-oil-ratio), the "bubble point" and the density of the oil, and in the case of gas type samples, measurement of the "dew point" of the gas phase, to produce the liquid deposit curve, or to perform a qualitative analysis of the gaseous mixture.

The invention comprises two coaxial radial cavities opening into the first chamber in the pointed part thereof, for an optical display assembly being two optical elements tightly inserted respectively in the two cavities, comprising each a rigid sleeve, a cylindrical block made of a transparent material such as sapphire arranged in line with the rigid sleeve and means for fastening an end of an optical fiber connected to a photoemission or photoreception element for forming the image of the end of the first chamber.

Using these optical fiber display blocks allows to automation of the phase separation operations with GOR determination with the aid of means for detecting the meniscus between the liquid phase and the gas phase of the sample.

According to a first embodiment, the two chambers are defined respectively by two rods forming pistons provided each with seals, the device comprising motive means for controlling the displacement of the two rods, and a gasometer placed in the thermostat-controlled enclosure, which contributes to shortening the interconnection circuits and to decreasing condensation risks, which are usually the cause of measuring errors.

According to the first embodiment the first chamber is defined by a rod forming a piston provided with seals, and the second chamber consists of the inner volume of a mobile piston gasometer placed on top of the first chamber.

In the first embodiment the cell and the gasometer are integrated which, provides a lighter device that can therefore be moved more easily on production sites, with a very short connection circuit between the cell and the gasometer, which favors precise measurements.

The body is fixed within the thermostat-controlled enclosure, the two mobile elements (and at least the rod in the first lower chamber in case it is topped by a gasometer) are respectively integral with two hangers that can each be shifted parallel to the two pistons by driving respectively into rotation threaded rods and the motive means (such as stepping motors or synchronous motors) for rotating the rods associated with each hanger separately or synchronously.

The piston of the gasometer slides for example in a cylinder and it is provided with a rod connected to motive means suited to limit the pressure in the cylinder to a set value, so as to be able to measure at this pressure the volume of gas released by the expansion of the mixture.

The invention preferably comprises a unit for controlling the motive means and the optical display block, comprising for example a module for controlling the motive means intended to drive the threaded rods and an optical coding measuring circuit intended to detect the motions transmitted to the threaded rods and to convert them into volume variation measurements, and optionally a module for controlling the illumination of the first chamber through the first optical element, and for forming the image of an interface between phases through the second optical element.

The invention can also comprise a vibrator for stirring the fluids in the first chamber, the control unit comprising a circuit producing the signal to be applied to the vibrator.

The invention advantageously comprises a micro-computer programmed to perform automatic measuring procedures.

The device comprises means for measuring the pressure at least in the first chamber, the control unit comprising a circuit for storing the calibration factors of these measuring means, as a function of a set temperature value associated with an element intended to select the calibration factors to be chosen as a function of this set temperature value assigned, in order to make the response of the measuring means independent thereof.

The pressure measuring means include at least one membrane pressure detector arranged in a cavity provided in the wall of the first chamber, the membrane being flush with the inner surface of this chamber so as to limit the clearance volumes.

The seals being mobile with the pistons, the clearance volumes between the two cylinders and the corresponding pistons remain substantially constant whatever their degree of penetration in their respective chambers.

The body is fixed within the thermostat-controlled enclosure, the two pistons are respectively integral with two hangers that can each be moved parallel to the two pistons by driving threaded rods respectively into rotation and motive means (stepping motors for example) for rotating separately the rods associated with each hanger.

The device preferably comprises a unit for controlling the motive means and the optical assembly.

This control unit comprises for example a module for controlling the motive means driving the threaded rods and an optical coding measuring system for detecting the motions transmitted to the threaded rods and for converting them into measurements of the concomitant volume variations of the two chambers. It can also comprise a module for controlling the illumination of the first chamber through the first optical element and for forming the image of an interface between fluid phases of the sample through the second optical element.

The device can also comprise a vibrator for stirring the fluids in the first chamber, and the control unit can also comprise a circuit producing a signal to be applied to the vibrator.

The device further comprises for example a means for measuring the pressure in the first chamber, the control unit comprising in this case a circuit for storing the calibration factors of this measuring means as a function of a set temperature value, associated with an element for selecting the calibration factors as a function of this set temperature value assigned, in order to make the response of the measuring means independent thereof.

The device preferably comprises a micro-computer programmed to perform automatic measuring procedures.

BRIEF DESCRIPTION OF THE DRAWINGS

Other features and advantages of the device according to the invention will be clear from reading the description hereafter of an embodiment given by way of non limiting example, with reference to the accompanying drawings in which:

FIG. 6 is a block diagram of the control unit associated with its control micro-computer.

DESCRIPTION OF THE PREFERRED EMBODIMENTS

Figure 1:
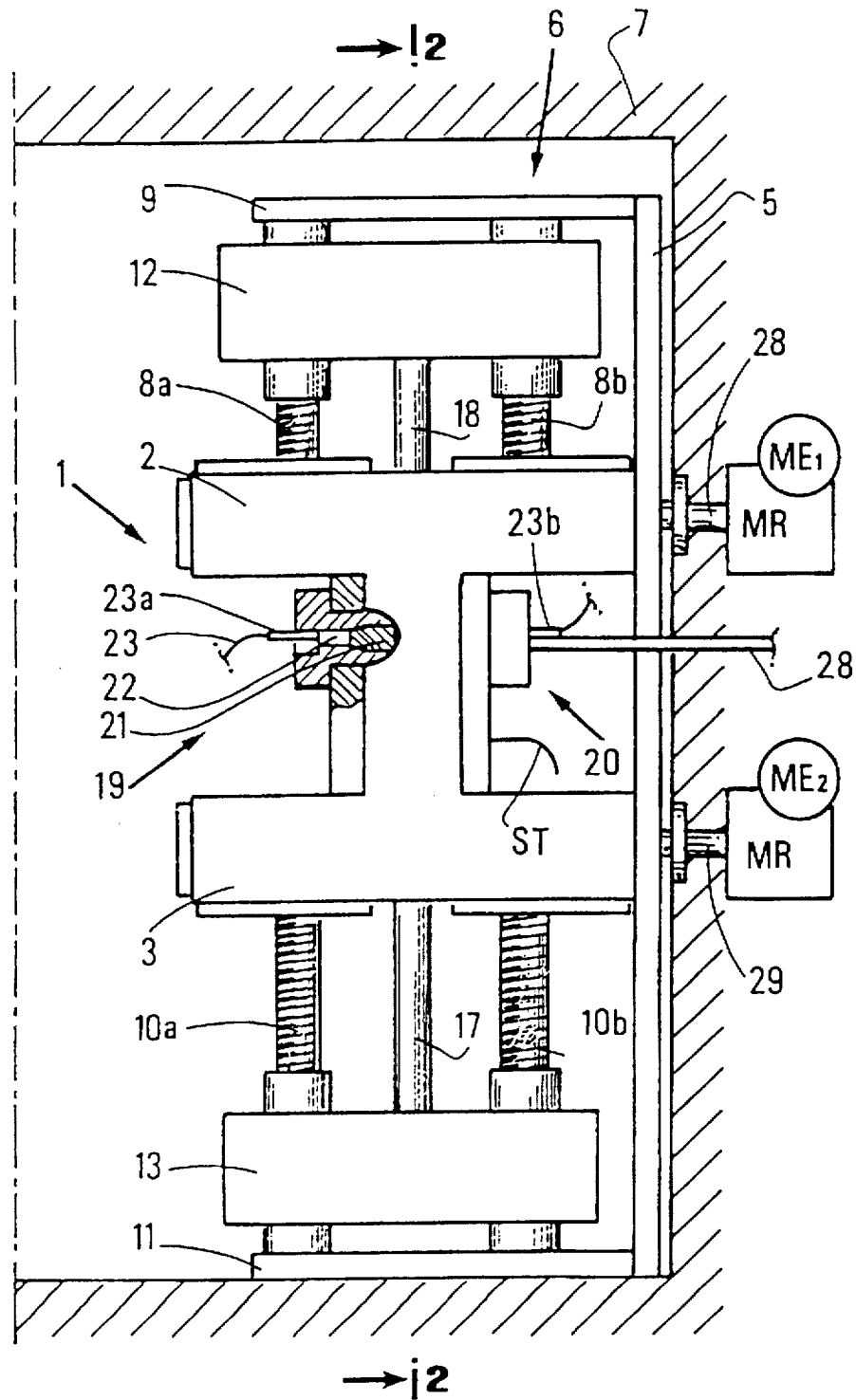
FIG. 1 diagrammatically shows a first cutaway view of an embodiment of the invention; in its thermostat-controlled enclosure.
Figure 2:
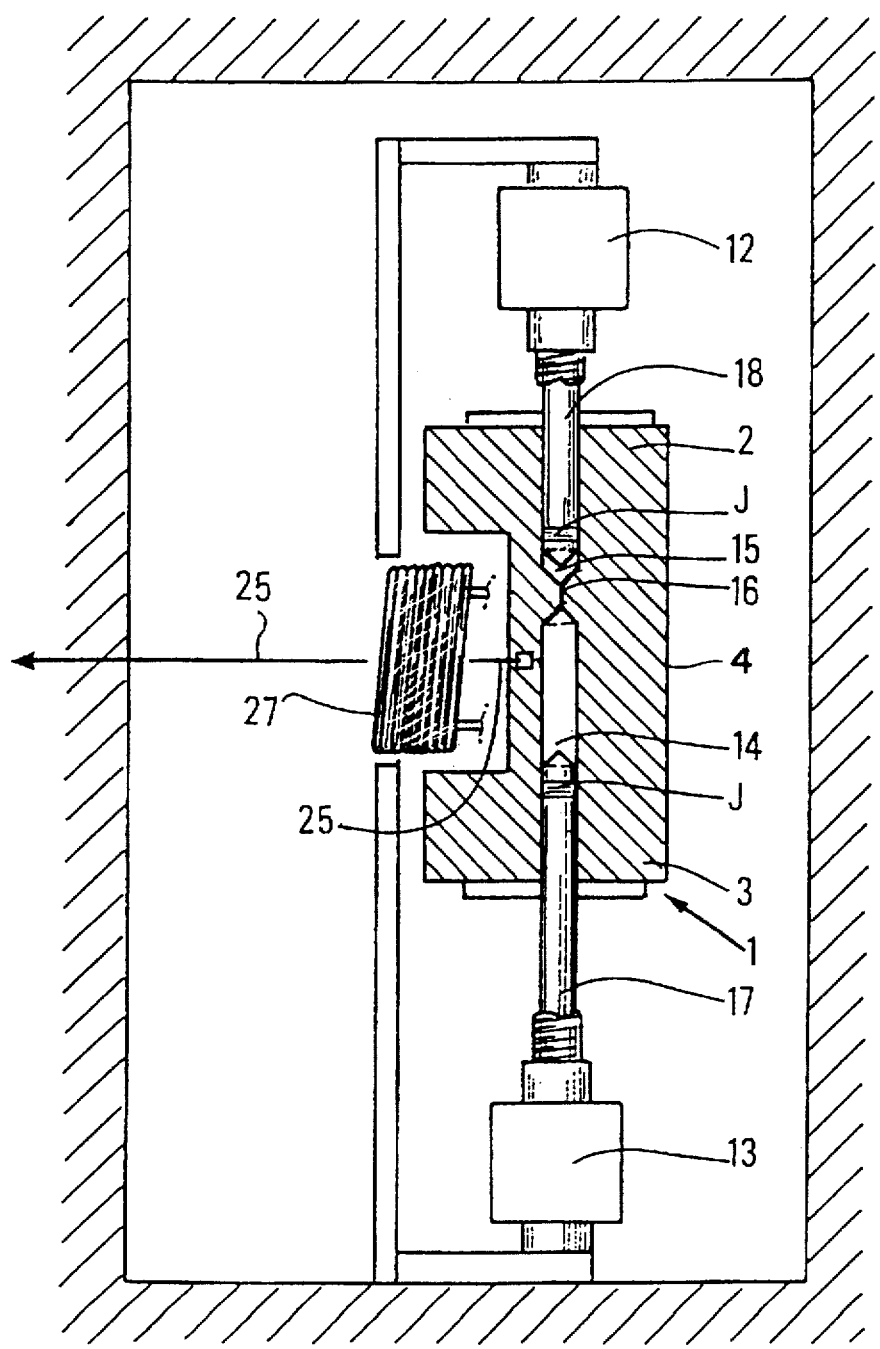
FIG. 2 diagrammatically shows another cutaway view of an embodiment of the invention.

The invention comprises (FIG. 1) a rigid body 1 having two plates 2 and 3 separated by a cylindrical block ST. The two plates of body 1 are fastened to a vertical post 5 of a rigid supporting frame 6. Body 1 is placed in a thermostat-controlled enclosure 7. Two threaded rods 8a, 8b set laterally apart from one another and rotating freely on their axis are arranged between an upper horizontal post 9 of frame 6 and the upper plate 2. Two similar rods 10a and 10b respectively in line with rods 8a and 8b are placed between the lower plate 3 of the body and another lower horizontal post 11 of frame 6.

Two hangers 12 and 13 are arranged on either side of body 1. They comprise threaded bores respectively suited to threaded rods 8, 10. The vertical translation of hangers 12, 13 is obtained by driving these threaded rods 8, 10 respectively into rotation.

Two coaxial cylindrical chambers 14 and 15 (FIGS. 2 to 5) with a conical bottom or end are provided through body 1. They communicate with each other at their points by means of a fine line 16 controlled by a valve V5. Two pistons 17 and 18 each provided with a conical end suited to the shape of the chambers slide in the two chambers. The two pistons are respectively integral with the two mobile hangers 12 and 13. Each one is provided with a seal J in the vicinity of its point. The peripheral clearance volume between each piston point and the corresponding seal J is thus constant whatever their degree of penetration in their respective chambers.

The device comprises an optical display assembly having (FIG. 1) two optical elements 19 and 20. Two coaxial radial cavities opening into the lower chamber 14 in the vicinity of its top are provided through body 1, respectively for the two optical elements 19 and 20. Each one of them has a metallic frame with a central bore for a transparent block 21, for example made from sapphire. Each block is externally extended by an optical fiber end 22. One of the optical fibers 23a communicates with a light source such as a photoemission diode for example, the optical fiber 23b of the opposite optical element 20 provided with a photoreception element allowing forming the image of the conical end of lower chamber 14.

With the particular conical-ended conformation of the draw-off zone at the top of the first chamber, with the sapphire block 22 and the illumination system, a very high precision is obtained for all the operations that are carried out on the fluids in the first chamber. This is the case in particular when all of the gas phase of a two-phase substance under pressure has to be drawn off with precision in this first lower chamber 14 and fed into the second chamber 15.

The body comprises a cavity opening onto the lower chamber 14 near the top thereof, for a pressure detector P1. A flush-membrane detector P1 (FIG. 7) is preferably used at least in the first chamber 14 so as to minimize the clearance lo volumes likely to affect the measuring accuracy. Conductors 25 connect detector P1 to a control unit situated outside the thermostat-controlled enclosure 7, which will be described in connection with FIGS. 4 and 6.

Furthermore, a temperature probe ST is placed in body 1 in the order to measure the temperature of the substance sample.

A piezoelectric ceramic (not shown) associated with an ultrasonic generator SU (FIG. 4) for stirring the substance sample fed into the first chamber 14 is fastened to the lower plate 3.

The two chambers 14 and 15 communicate respectively, by means of valves V2, V4, with a capillary pipe coil 27 (FIG. 5) allowing transfer of fluid from one chamber to the other and to perform viscosity measurements. A valve V3 communicating with the fine line 6 between the two chambers 14 and 15 allows the lower chamber 14 to be drained. A valve V1 controls access to the lower chamber 14 for delivering fluid samples to be analyzed.

Figure 3:
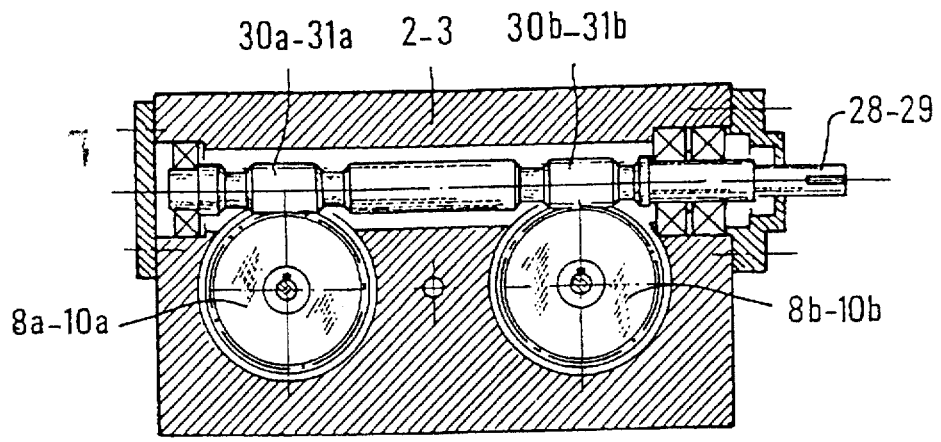
FIG. 3 diagrammatically shows a cutaway view of the means for driving the threaded rods into rotation.

A driving shaft 28 and 29 arranged in a perpendicular plane with respect to the axes of the threaded rods is respectively associated with each pair of threaded rods 8a and 8b and 10a and 10b (FIG. 3). Each shaft is secured to one of the plates 2 and 3 but it can rotate on its axis. Each one of them bears two gears 30a and 31a on the one hand and 30b and 31b on the other, that mesh with the threads of the corresponding rods 8 and 10. The external ends of shafts 28 and 29 are each coupled with a driving stepping motor ME1 and ME2 (FIG. 1) in a housing adjacent to the thermostat-controlled enclosure.

The device also comprises a control unit CA (FIG. 6) including:

- a module 32 for controlling the two driving motors ME1, ME2 and an optical coding measuring circuit 33 for detecting the motions transmitted to the driving shafts 28 and 29 of motors ME1 and ME2 and for converting them into measurements of the concomitant volume variations of the first and of the second chamber 14 and 15;
- a circuit 34 for regulating the temperature. This circuit receives temperature data from probe ST. It acts on heating elements 35 of the thermostat-controlled enclosure and it is suited to limit automatically the maximum temperature prevailing therein;
- a module 36 for controlling the illumination of the lower chamber 14 through porthole 19 and for receiving the image of the interface between the phases received through porthole 20;
- a circuit 37 producing the signal to be applied to ultrasonic generator SU;
- a circuit 38 for storing the calibration factors of pressure detector 26 as a function of the set temperature value indicated by temperature probe ST, associated with an element 39 for selecting the calibration factors to be chosen as a function of the set temperature value assigned, in order to make the response of detector 31 independent thereof. The control unit also comprises circuits 40 and 41 for detecting the position of the hangers with end-of-travel indicators, as well as a detection circuit 42 connected to pressure detectors P1 and P2 for detecting an excess of pressure in the chambers above a set pressure value.

A micro-computer 43 is associated with the control unit for running automatically the measurement sequences.

The section of chambers 14 and 15 is small enough to allow tests to be carried out with small substance volumes, of the order of some $cm^3$, and the motive means are suited to bring the pressure in these chambers to several hundred bars, by shifting the rods 17 and 18 forming pistons. The small volumes used allow to minimizing safety problems on the one hand and the duration of the previous heating and stirring stages on the other hand.

The substance sample being submitted to the temperature and pressure conditions prevailing in the underground zone where it was taken, its pressure can at first be lowered by moving back the first piston 17 sufficiently to be able to measure its compressibility for example. Lowering its pressure even further leads to the partial vaporization thereof. By opening valve V5, all of the gas phase can be transferred into the second chamber 15.

Figure 5:
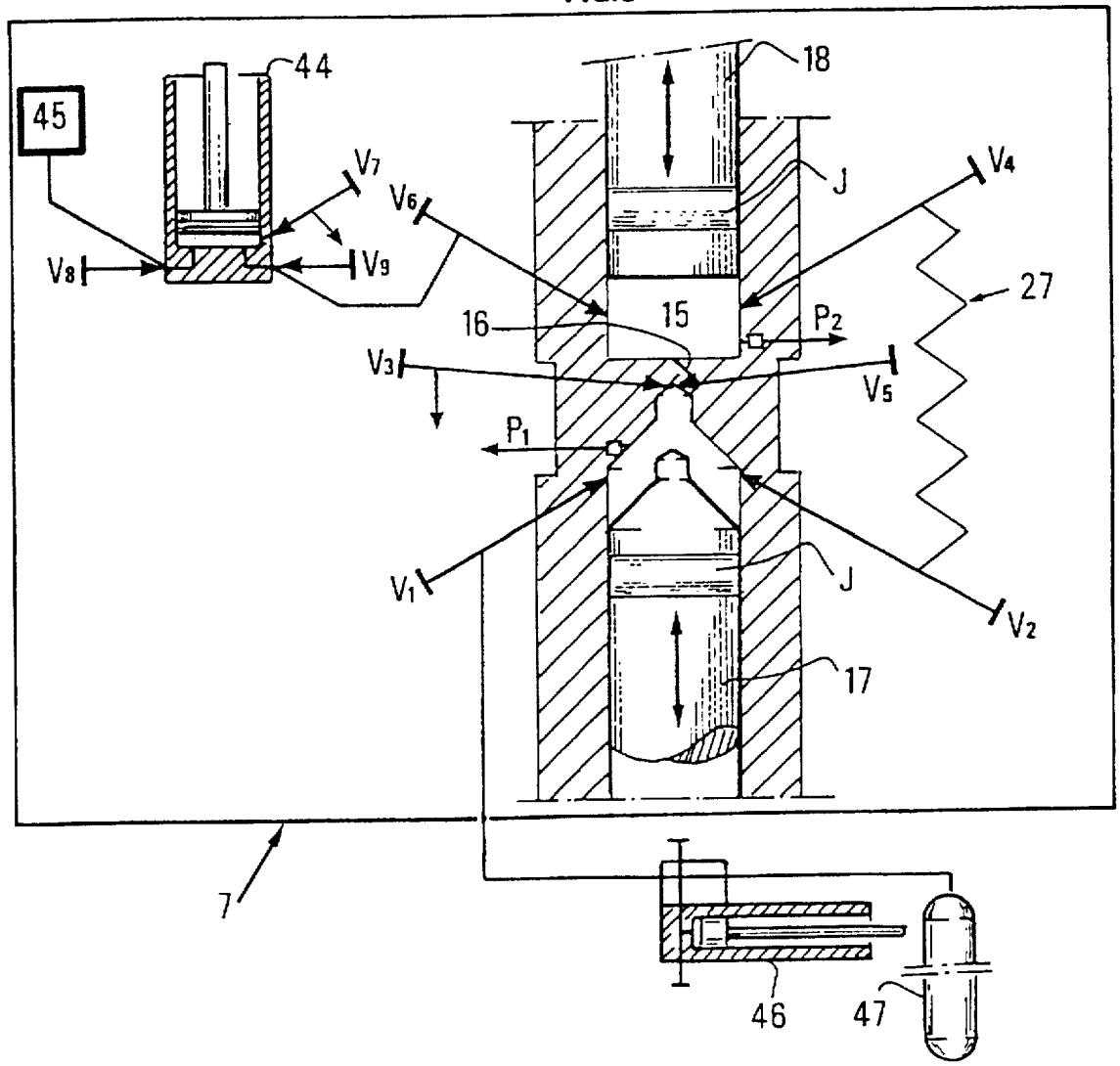
FIG. 5 diagrammatically shows a first implementation mode of the the invention suited for thermodynamic measurements on fluid samples.
Figure 4:
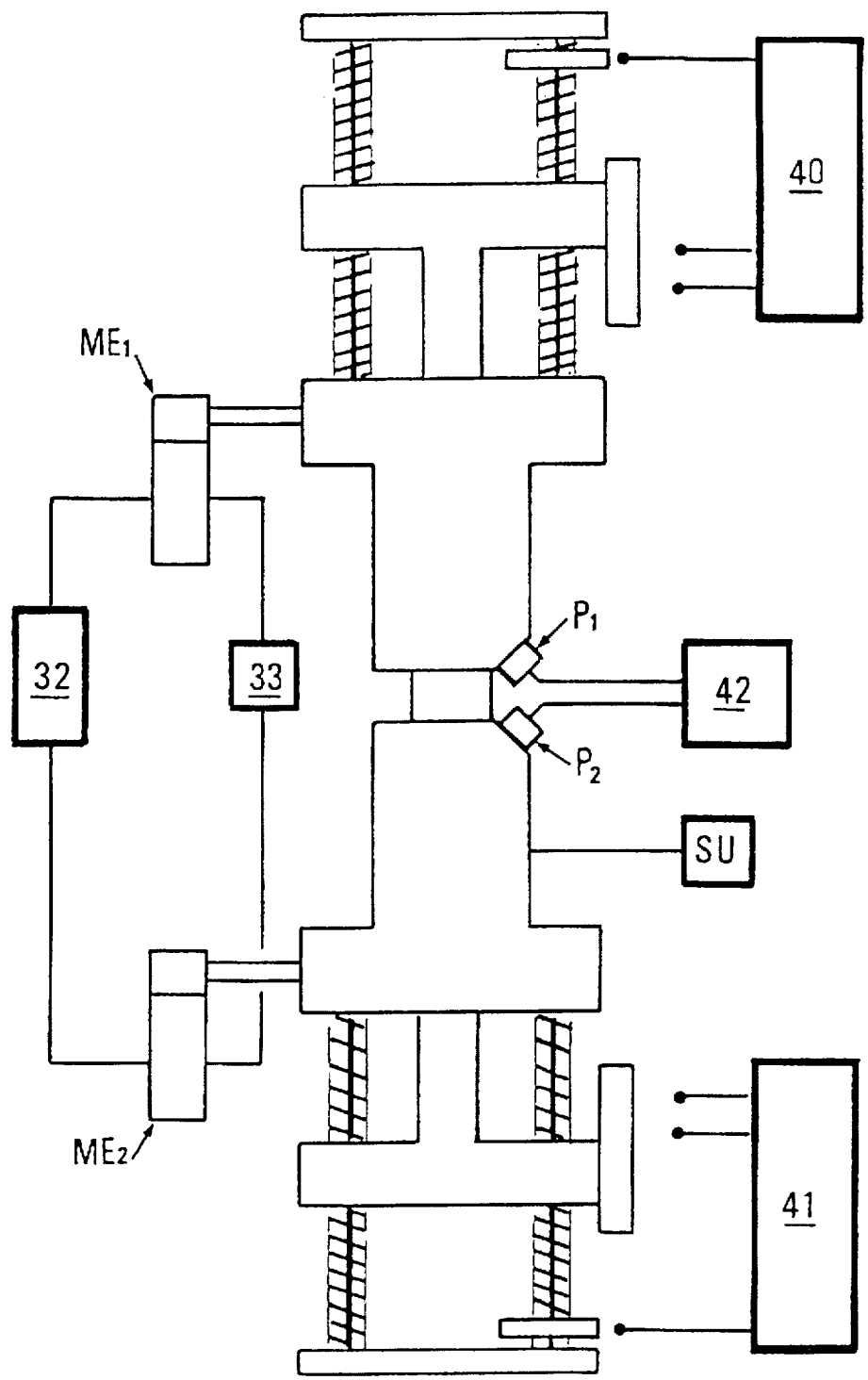
FIG. 4 diagrammatically shows the invention associated with control modules.

According to the implementation mode of FIG. 5, the device is associated with a gasometer 44 that is arranged in the climatic enclosure 7 in proximity to the body 1 of the cell. An inlet of the gasometer controlled by a valve V9 is connected to the second chamber 15 by valve V6.

The gasometer can be connected to a vacuum pump (not shown) by a valve V7. This gasometer 44 allows measurement of the volume of the gas taken in the second chamber after expansion to atmospheric pressure. This proximity of chamber 15 and gasometer 44 and their maintenance at the same temperature, which prevents condensation, allows preciser measurements to be performed.

The gasometer is coupled for example with a chromatography apparatus 45 by means of a valve V8. The first chamber can be coupled, by means of valve V1, with a draw-off microcell 46 of a well-known type in order to measure the density of the substance studied.

Pressure transfer of a sample into the first chamber of the device can also be achieved directly from a transport bottle 47. It can also be fed into microcell 46 at an intermediate stage, prior to transferring it into the first chamber 17. The microcell can be weighed in order to determine the mass fed into the cell. The density of the substance can also be determined.

The embodiment of FIG. 5 is particularly well suited for thermodynamic studies on samples while measuring the viscosity for example by coupling chambers 15 and 17 by means of coil 27. If it is only desired to validate a sample to check that it is really representative of the substances to be analyzed, the device is used for example according to the embodiment of FIG. 7.

Figure 7:
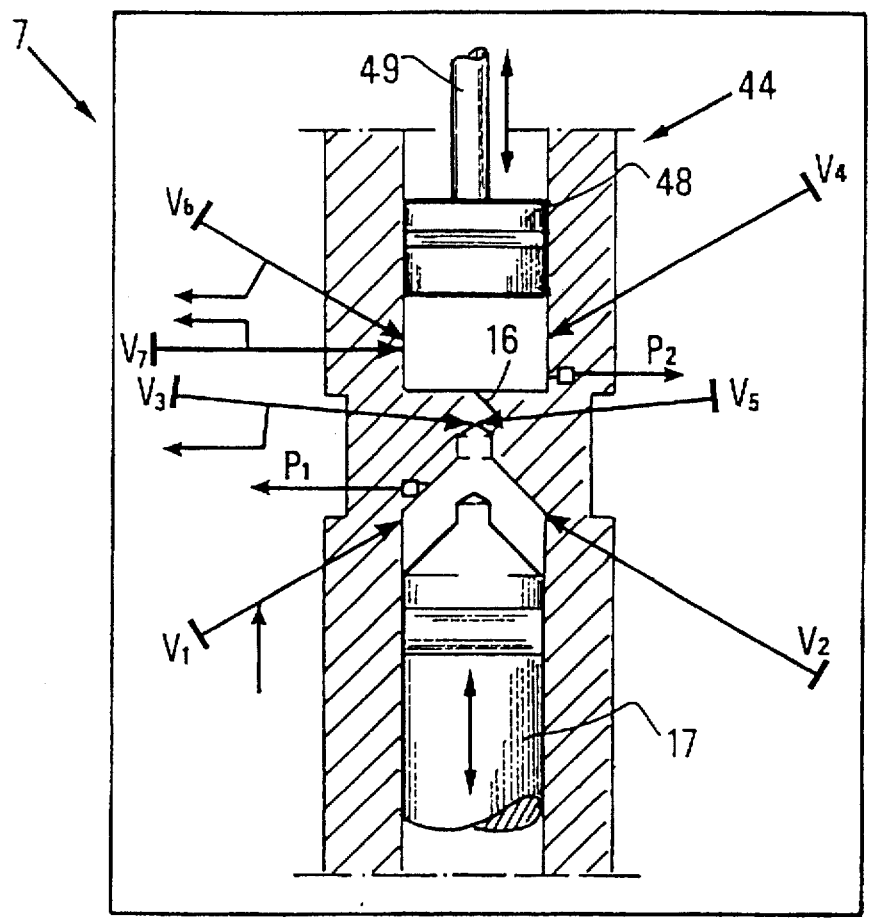
FIG. 7 diagrammatically shows a second implementation mode of the device suited for the validation of fluid samples.

In FIG. 7, it can be seen that the second chamber has the inner volume of a gasometer such as 44. The rod 18 coupled with the motive means (8, 12, ME1) is here replaced by a piston 48 sliding in a cylinder 49. The rod of this piston is connected to motive means suited to maintain the pressure in cylinder 49 at most equal to a reference value, so as to be able to measure at this pressure the volume of gas released by the expansion of the mixture. Similarly, this gasometer is placed in the thermostat-controlled enclosure 7 for a higher measuring precision.

With this layout where the cell and the gasometer are integrated, a lighter device is obtained, that can be more easily moved on production sites. Besides, the circuit connecting the cell to the gasometer is very short, which eliminates a known cause of measuring inaccuracy.

Micro-computer 43 is suited to perform certain acquisition and operation control sequences. It performs for example an automatic pressure control when, at a given set temperature value, the gas is transferred from the second chamber to gasometer 44 by being expanded to atmospheric pressure, in order to determine its volume under standard conditions (a correction is introduced to give the volume at 15° C.). It also programs the set temperature value to be met. At the operator's demand, it carries out an acquisition of the measured pressure, volume and temperature (P, V, T) data.

Micro-computer 43 can also conduct an automatic decompression sequence with successive stabilizations at several pressure stages. In this case, it scans the pressure and waits for its stabilization to carry out the acquisition of the P, V, T data prior to a new decompression.

At the operator's demand, micro-computer 43 can also carry out all the necessary P, V, T measurements and acquire them after validation, whether it be the pressure at the set temperature value, the determination of the volumes of the fluids contained in the first and in the second chamber at a set temperature and pressure value, of the volume of the gas phase obtained at ambient temperature and atmospheric pressure.

The Micro-computer 43 comprises a storage means for recording the data acquired.

By means of programming, micro-computer 43 can be made to carry out a certain number of different operations according to whether the embodiment of FIG. 5 is used to determine thermodynamic parameters of the sample studied and/or calibration parameters, or the embodiment of FIG. 7 is used for sample for validation operations.

We claim:

1. A device for determining, on a production site, physical characteristics of fluid samples extracted from a subsoil such as from petroliferous areas, comprising, in a thermostatically-controlled enclosure, a body including a first chamber and a second chamber arranged above the first chamber, the first chamber comprising a pointed end, a first mobile element and a second mobile element for varying volumes of the first and second chambers, a shifting device for shifting the first and second mobile elements, a valve for transferring fluids to or from the first and second chambers, and a controlled communication between the first and second chambers, wherein the body comprises two coaxial radial cavities opening into the first chamber at the pointed end, for an optical display assembly having first and second optical elements inserted respectively into the two coaxial radial cavities, each comprising a rigid sleeve, a cylindrical block made of a transparent material placed in line with the rigid sleeve and means for fastening an end of an optical fiber connected to a photo-emission or photo-reception element, for forming an image of the pointed end of the first chamber.

2. A device as claimed in claim 1, wherein the first and second mobile elements include a first rod and second rod each provided with seals and respectively being displaceable in the first and second chambers, and further comprising a first motor for controlling the displacement of the first and second rods, and a gasometer provided with a piston placed in the thermostatically-controlled enclosure.

3. A device as claimed in claim 2, further comprising:
two hangers and wherein the body is fixedly positioned in the thermostatically-controlled enclosure, the first and second rods are respectively integral with the two hangers, the shifting device includes rotatable threaded rods parallel to the two rods and arranged for displacing the two hangers when rotated, a motor driving separately and synchronously the first and second threaded rods in rotation.

4. A device as claimed in claim 3, further comprising:
another motor for displacing the piston in the gasometer and a limiter for limiting pressure in the gasometer to a set pressure, thereby enabling the volume of gas released by the expansion of the mixture to be measured at the set pressure.

5. A device as claimed in claim 3, wherein the shifting device includes one of stepping or synchronous motors.

6. A device as claimed in claim 3, comprising:
a control unit for controlling the shifting device and the optical display assembly.

7. A device as claimed in claim 2, further comprising:
a hanger and wherein the body is fixedly positioned in the thermostatically-controlled enclosure, the first rod is integral with the hanger, the shifting device includes rotatable threaded rods parallel to the first rod and arranged for displacing the hanger when rotated, the shifting device driving the threaded rods in rotation.

8. A device as claimed in claim 7, further comprising:
a motor for displacing the piston in the gasometer and a limiter for limiting pressure in the gasometer to a set pressure, thereby enabling the volume of gas released by the expansion of the mixture to be measured at the set pressure.

9. A device as claimed in claim 7, wherein the shifting device includes one of stepping or synchronous motors.

10. A device as claimed in claim 7, comprising:
a control unit for controlling the shifting device and the optical display assembly.

11. A device as claimed in claim 7, comprising:
a control unit including a module for controlling the first motor and an optical coding measuring circuit for detecting rotation of the threaded rods and for converting detected rotation into volume variation measurements.

12. A device as claimed in claim 11, comprising:
a vibrator for stirring fluids in the first chamber and wherein the control unit includes a driving device for the vibrator.

13. A device as claimed in claim 11, comprising a pressure sensor for measuring pressure in the first chamber, the control unit comprising a circuit for storing calibration factors of the pressure sensor as a function of a set temperature value, a selecting element associated with the first circuit for selecting calibration factors to be chosen as a function of the set temperature value, to make a response of the pressure sensor independent of the temperature.

14. A device as claimed in claim 2, comprising:
a control unit for controlling the shifting device and the optical display assembly.

15. A device as claimed in claim 2, comprising a viscosity measuring device connected between the first and second chamber.

16. A device as claimed in claim 1, wherein:
the gasometer is placed on top of the first chamber, the first and second mobile elements including a rod and the piston, the rod being provided with seals and displaceable in the first chamber and the piston being displaceable in the gasometer for varying volume thereof.

17. A device as claimed in claim 16, further comprising:

a motor for displacing the piston in the gasometer and a limiter for limiting pressure in the gasometer to a set pressure, thereby enabling the volume of gas released by the expansion of the mixture to be measured at the set pressure.

18. A device as claimed in claim 17, comprising:

a control unit including a module for controlling the motor and an optical coding measuring circuit for detecting rotation of the threaded rods and for converting detected rotation into volume variation measurements.

19. A device as claimed in claim 16, comprising:

a control unit for controlling the shifting device and the optical display assembly.

20. A device as claimed in claim 1, comprising:

a control unit for controlling the shifting device and the optical display assembly.

21. A device as claimed in claim 20, wherein the control unit comprises a module for controlling illumination of the first chamber by the photo-emission element through the first optical element, and for forming an image of an interface between phases of the fluid samples through the second optical element.

22. A device as claimed in claim 21, comprising:

a vibrator for stirring fluids in the first chamber and wherein the control unit includes a driving device for the vibrator.

23. A device as claimed in claim 21, comprising a pressure sensor for measuring pressure in the first chamber, the control unit comprising a circuit for storing calibration factors of the pressure sensor as a function of a set temperature value, a selecting element associated with the first circuit for selecting calibration factors to be chosen as a function of the set temperature value, to make a response of the pressure sensor independent of the temperature.

24. A device as claimed in claim 20, comprising:

a vibrator for stirring fluids in the first chamber and wherein the control unit includes a driving device for the vibrator.

25. A device as claimed in claim 20, comprising a pressure sensor for measuring pressure in the first chamber, the control unit comprising a circuit for storing calibration factors of the pressure sensor as a function of a set temperature value, a selecting element associated with the first circuit for selecting calibration factors to be chosen as a function of the set temperature value, to make a response of the pressure sensor independent of the temperature.

26. A device as claimed in claim 25, wherein the pressure sensor includes at least one membrane pressure detector arranged in a cavity provided in the wall of the first chamber, the membrane being flush with an inner surface of the first chamber so as to limit clearance volumes.

27. A device as claimed in claim 20, comprising a micro-computer programmed to perform automatic measurement procedures.

* * * * *